United States Patent [19]

Goetz et al.

[11] 4,043,668

[45] Aug. 23, 1977

[54] PORTABLE REFLECTANCE SPECTROMETER

[75] Inventors: Alexander F. H. Goetz, Altadena; Richard A. Graham, La Crescenta; Tetsuo Ozawa, Gardena, all of Calif.

[73] Assignee: California Institute of Technology, Pasadena, Calif.

[21] Appl. No.: 561,369

[22] Filed: Mar. 24, 1975

[51] Int. Cl.$^2$ .............................. G01J 3/48
[52] U.S. Cl. .................... 356/73; 250/339; 356/74; 356/188; 356/189
[58] Field of Search ............. 356/51, 74, 83, 84, 356/96–98, 73, 76, 188; 250/338–342, 351, 372, 226

[56] References Cited

U.S. PATENT DOCUMENTS

| 3,398,285 | 8/1968 | Sachs | 356/82 X |
|---|---|---|---|
| 3,409,772 | 11/1968 | Wormser | 356/51 X |
| 3,715,163 | 2/1973 | Mitchell | 356/97 X |
| 3,860,818 | 1/1975 | Stalder et al. | 356/51 X |
| 3,864,037 | 2/1975 | Johnson | 356/74 |
| 3,923,399 | 12/1975 | Brumley | 356/96 |

FOREIGN PATENT DOCUMENTS 626,425 8/1961 Canada ................ 356/76

OTHER PUBLICATIONS

Goldberg, SPIE Journal, vol. 9, Nov., 1970, pp. 22-31.

*Primary Examiner*—John K. Corbin
*Assistant Examiner*—F. L. Evans
*Attorney, Agent, or Firm*—Eric T. S. Chung

[57] ABSTRACT

A portable reflectance spectrometer is disclosed. The spectrometer essentially includes an optical unit and an electronic recording unit. The optical unit includes a pair of thermoelectrically-cooled detectors, for detecting total radiance and selected radiance projected through a circular variable filter wheel, and is capable of operating to provide spectral data in the range 0.4 $\mu$m to 2.5 $\mu$m without requiring conventional substitution of filter elements. The electronic recording unit essentially includes power supplies, amplifiers, and digital recording electronics designed to permit recordation of data on tape casettes. Both the optical unit and electronic recording unit are packaged to permit carriage as backpack items and thereby be manually portable.

10 Claims, 4 Drawing Figures

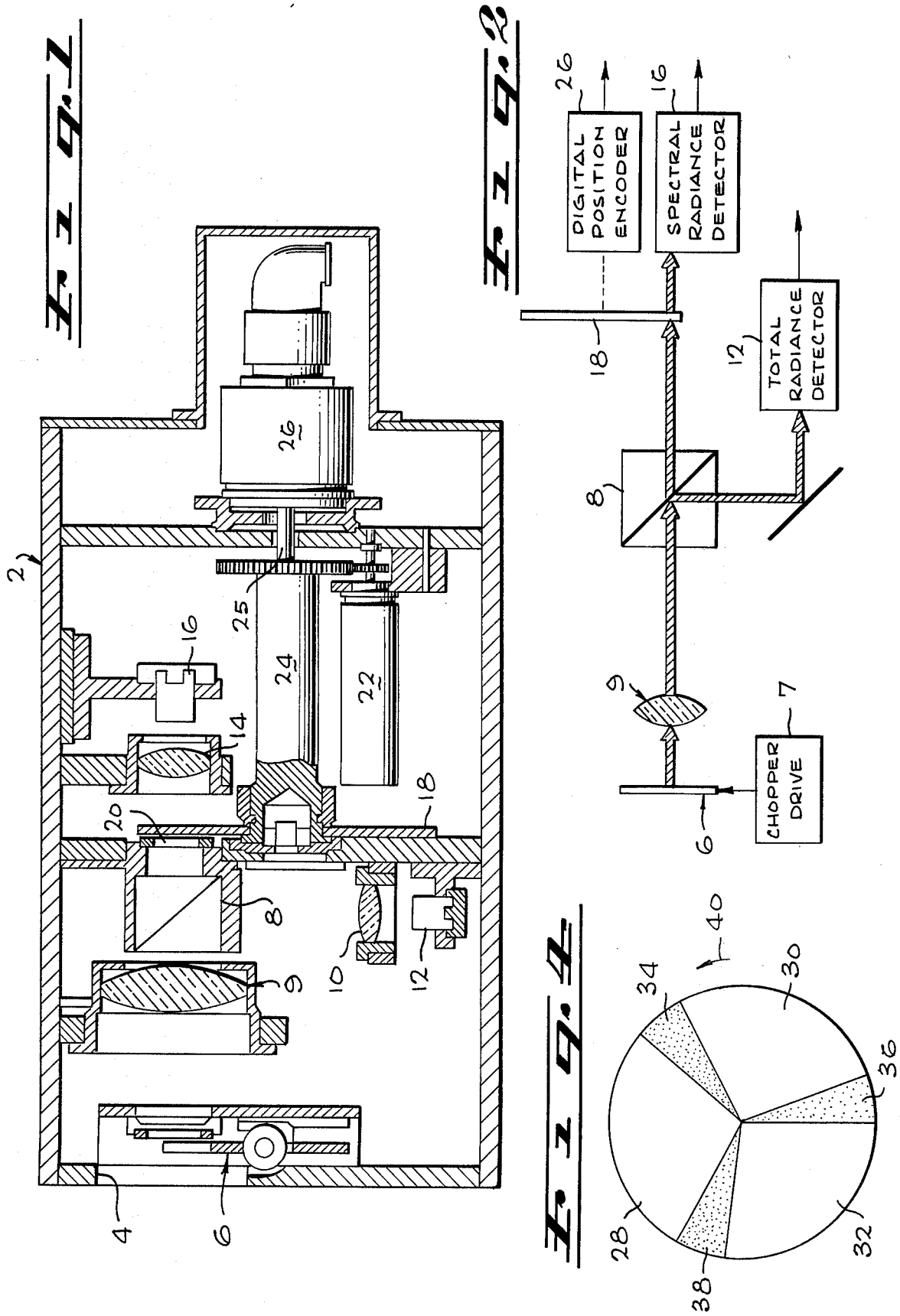

PORTABLE REFLECTANCE SPECTROMETER

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435: 42 USC 2457).

BACKGROUND OF THE INVENTION

1. Field of the Invention

This invention generally relates to spectrometers. More specifically, the present invention concerns a portable reflectance spectrometer that is capable of being manually carried for use in obtaining spectral data at remote geographical locations.

2. Description of the Prior Art

Satellite technology today makes possible geographical surveys of the earth's surface by means of satellite-carried systems. As an example, the earth resources technology satellite (ERTS) produces images of the earth's surface in four spectral bands with an instantaneous field of view of approximately 79 meters, i.e., the approximate size of a football field. As a further example, the Skylab multispectral scanner produces images in thirteen spectral bands with a picture element size generally similar to that of the earth resources technology satellite.

Direct identification of earth materials by using spectral methods requires that satellite images be calibrated to one or more known points within the image.

To get a true measure of the average spectral reflectance for an area covered by a picture element, as many as 100 spectra are required to obtain a statistical average of the reflectance for an area. The effects of varying atmospheric transmittance and sky radiance also must be accounted for during a spectral scan. It is highly desirable to have a portable spectrometer which is manually portable so as to be capable of being used in a light aircraft or best of all manually carried to remote areas covered within a picture element being simultaneously surveyed by a satellite-carried system. With such a manually portable spectrometer, true values for the reflectance for a calibration area of a picture element can be determined from data obtained at or near ground level. It would then be possible to readily design image processing procedures to effectively normalize image data to the calibration area and make accurate determination of rock and soil types at other points in the picture covered by the satellite-carried system. This is particularly important in the area of searching for particular mineral deposits and/or areas of hydrothermal alteration and the like.

The prior art includes numerous different types of spectrometers. Prior art reflectance-type spectrometers, however, have generally not been suitable for use in obtaining measurements in remote areas, for the reason that such systems have been extremely complex and large, typically being required to be transported in trucks and/or vans. Accordingly, spectral data for remote areas has not been heretofore readily obtained at ground levels. Moreover, typical prior art spectrometers have been limited to use for a narrow spectral range generally spanning approximately a third of the spectral range covered by the subject invention.

Accordingly, the potential for accurate accumulation and recordation of spectral data has been in the past severely limited and has effectively denied scientists the ability of properly analyzing the vast amount of information that is actually obtained through the ERTS satellite and similar satellite-carried systems.

It is, therefore, the intention of the present invention to provide a portable reflectance spectrometer which is capable of being readily manually carried such that accurate spectral reflectance information of remote areas representing calibration areas can be obtained to enable the valid interpretation of spectral picture elements obtained by satellite systems.

OBJECTS AND SUMMARY OF THE INVENTION

Accordingly, it is a object of the present invention to provide a manually portable reflectance spectrometer that is capable of obtaining spectral data over a wide range without any requirement for physically changing filter elements.

It is a further object of the present invention to provide a portable reflectance spectrometer system that permits correlative spectral data to be obtained simultaneously with the overhead passage of a satellite survey system.

It is a yet further object of the present invention to provide a reflectance spectrometer system including means for automatically digitally recording spectral data at locations where spectral measurements are being taken.

It is a still further object of the present invention to provide a reflectance spectrometer system in which digital data is recorded on tape carried in casettes to permit easy playback and storage at a permanent facility.

Briefly described, the present invention involves a portable reflectance spectrometer that is manually transportable to permit the accumulation and recordation of spectral data at field locations.

More particularly, the subject portable reflectance spectrometer essentially includes an optical unit and an electronics unit. The optical unit includes a circular variable filter wheel which, when rotated, enables the cyclical detection of spectral data in three contiguous spectral regions. A pair of detectors are included in the optical unit to allow the collection of desired spectral data and for obtaining a measurement of total radiance. The electronics unit includes appropriate power supplies, amplifier circuits and digital recordation circuitry.

Further objects and the many advantages of the subject invention will be more readily appreciated as the same becomes better understood by reference to the following detailed description which is to be considered in connection with the accompanying drawings wherein like reference symbols designate like parts throughout the figures thereof.

BRIEF DESCRIPTION OF THE DRAWINGS

FIG. 1 is a schematic diagram illustrating a cross-sectional planar view of an exemplary optical unit that is suitable for use in accordance with the present invention.

FIG. 2 is a functional block diagram illustrating the essential components of the optical unit shown in FIG. 1.

FIG. 4 is a schematic diagram illustrating a circular filter wheel that is usable in accordance with the present invention.

DETAILED DESCRIPTION OF THE PREFERRED EMBODIMENT

Figure 3:
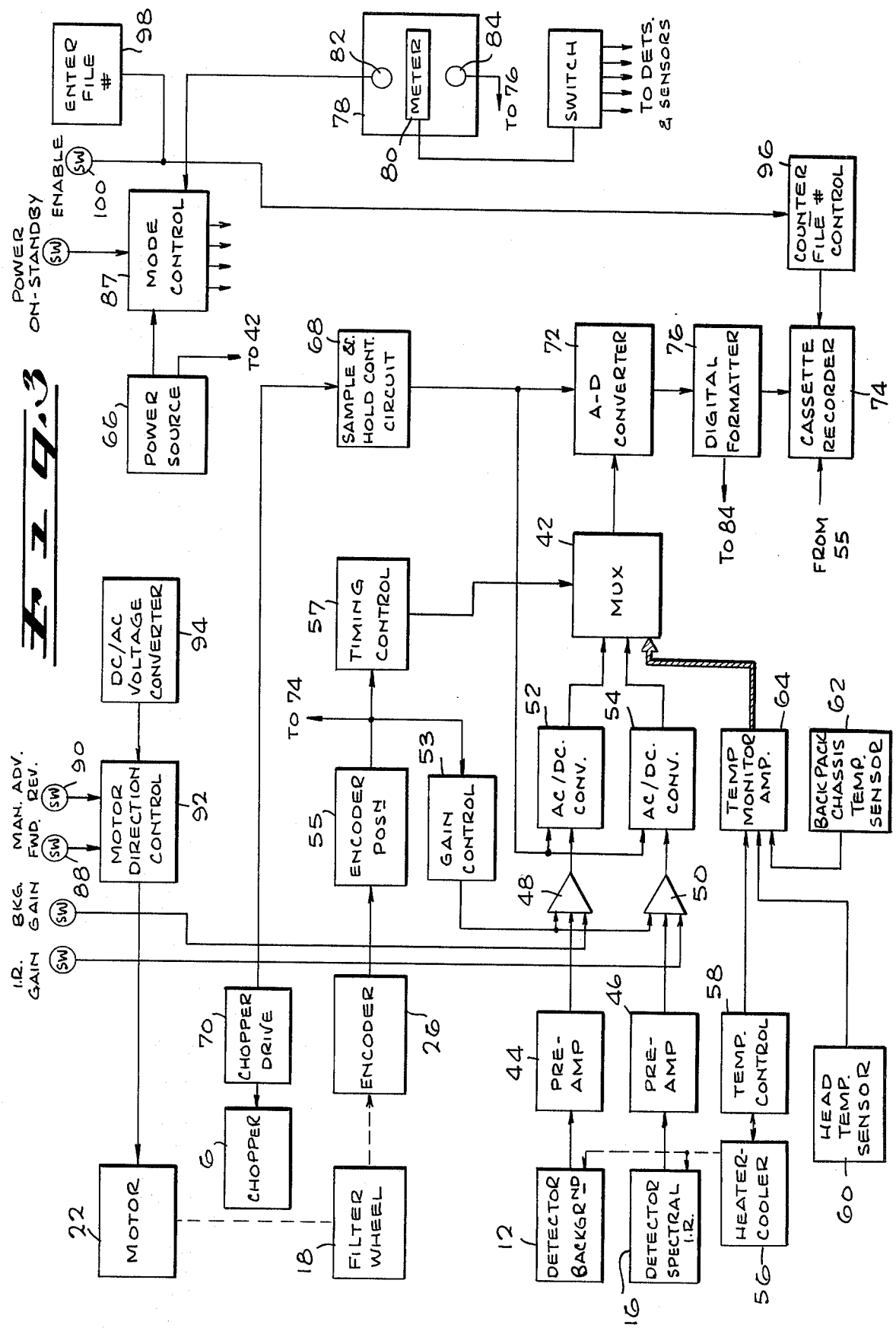
FIG. 3 is a schematic block diagram illustrating an electronics unit that is suitable for use in accordance with the present invention.

Referring to FIGS. 1 and 2 of the drawings, an optical unit in accordance with the present invention is illustrated. As shown, the optical unit is enclosed by a housing 2 which is provided with a frontal aperture 4 through which reflected radiation is permitted to enter the optical system. A vibrating reed chopper 6 is positioned at the aperture to effectively interrupt incident radiation. The reed chopper 6 may be driven by a conventional drive unit 7. Incident radiation is chopped to effectively provide an AC signal. As is well known, use of an AC signal rather than a DC signal eliminates difficulties produces by low frequency noise and permits avoidance of problems that are typically attendant to DC amplification.

The chopped radiation is allowed to be projected through a relay lens assembly 9 to a beam splitter 8, such that a portion of said incident radiation is directed through a condensing lens 10 to a lead sulfide (PbS) detector 12 which serves to provide a signal representative of total field or source radiation. A portion of said incident radiation is also projected through the beam splitter 8 and a second condensing lens assembly 14 to a second lead sulfide (PbS) detector 16 that is positioned to provide output signals representative of pre-determined spectral radiation that is transmitted through a circular variable filter 18. A slit 20 is positioned to mask the filter from incident radiation to provide greater spectral selectivity.

The circular variable filter 18, when the invention is operated in a Automatic mode, may be rotated at a rate of 2 revolutions per minute by the use of a suitable conventional drive motor 22 that is operatively connected to a drive shaft and gear assembly 24 to which the filter wheel is secured to be revolved. A connecting shaft 25 is connected to a digital shaft encoder 26 which serves to provide output signals indicative of the position of the filter wheel.

Referring to FIG. 2, operation of the optical unit may be readily understood to involve incident radiation being chopped by the chopper assembly 6 which is then projected through the relay lens 9 to the beam splitter 8. Portions of the incident radiation are thereby directed onto a background detector 12 and a spectral radiance detector 16. The spectral radiance is first projected through the variable filter wheel 18 whose position and hence the wavelength of radiation passed through the filter is indicated by signals provided from the digital shaft encoder 26.

Thermoelectric temperature control of the detectors 12 and 16 to 15° ± 0.02° C allows the subject invention to be operated in a 0° to 50° C environment. Stabilizing the detector temperatures eliminates a major source of signal drift.

Referring briefly to FIG. 4, a circular variable filter wheel in accordance with this present invention may include three filter segments 28, 30 and 32 which are separated by opaque segments 34, 36 and 38. The filter segments 28, 30 and 32 collectively serve to cover the range of 0.4$\mu$m to 2.5$\mu$m. As shown, the filter segment 28 may be designed to progressively permit the passage therethrough of radiation having wavelengths in the range of 0.4$\mu$m to 0.7$\mu$m. Similarly, the filter segment 30 may be designed to permit passage therethrough of radiation having wavelengths in the range of 0.7$\mu$m to 1.4$\mu$m. The third filter segment 32 would be designed to permit spectral radiation having wavelengths in the range of 1.4$\mu$m to 2.5$\mu$m to be passed therethrough. The range of wavelengths covered by the respective filter elements 28, 30 and 32 may overlap to avoid any wavelength coverage gap.

Assuming that the filter wheel 18 is rotated in a counterclockwise direction, such as is indicated by the arrow 40, spectral radiance would be permitted to be passed through each of the portions of the respective filter segments 28, 30 and 32 twice per minute or once every thirty seconds. In the event that the subject invention is operated in a Manual mode, the filter wheel 18 would be placed in any desired position to continually permit passage of radiation having a single selected wavelength. The respective opaque segments 34, 36 and 38 are used in accordance with the present invention to permit the recordation of miscellaneous measurements such as power supply voltages and selected temperatures.

As is later explained, recordation is accomplished digitally and may be in the form of multi-bit words, each such word may for example include up to 48 bits and may constitute several data words including a file number, the gain of signal amplifiers, filter wheel position and the respective detector output signals.

The spectral selectivity of recorded data would be dependent on the number of encoder positions used. As an example, 512 positions may be used satisfactorily wherein the opaque sections may be, depending upon the size of the respective filter segments 28, 30 and 32, in the neighborhood of 43 positions in arcuate width corresponding to approximately 30 degrees. Generally only the center 10 degrees portion of each opaque segment is required to be used for recordation of miscellaneous measurements. Each of the filter segments may generally have the same arcuate dimensions.

Referring now to FIG. 3, an exemplary recording electronics unit suitable for use with the subject invention is illustrated. Signals from the respective detectors 12 and 16 are applied to amplifier-demodulator channels prior to being applied to a multiplexer 42.

The respective amplifier-demodulator channels include pre-amplifiers 48 and 50 and AC-to-DC voltage converters 52 and 54. The AC-to-DC voltage converters serve to have the AC signals provided as output signals from the detectors 12 and 16 converted to DC signals for recordation purposes.

The gain of the respective amplifiers 48 and 50 included in the amplifier-demodulator for the detectors 12 and 16 are controlled by a gain control circuit 53 in response to signals derived from the digital shaft encoder 26 via an encoder position circuit 55 which may simply be a conventional circuit that provides an electrical signal representative of the physical position of the filter wheel 18 in accordance with the output from the encoder 26. The purpose for such gain control circuit 55 is to effectively enable a decrease in the gain of the amplifiers 48 and 50 whenever spectral radiation having wavelengths in the range of 1.4$\mu$m to 2.5$\mu$m accommodated by filter segment 32, is incident on the detector 16. The requirement for such decrease in gain is due to lead sulfide detectors being more highly sensitive to radiation having wavelengths in the range of 1.4$\mu$m to 2.5$\mu$m as compared to radiation having wavelengths in the range 0.4$\mu$m to 1.4$\mu$m which are accommodated by filter segments 28 and 30 of the filter wheel 18.

Gain control of the amplifiers 48 and 50 by the gain control circuit 55 is readily accomplished by simply detecting whenever the filter wheel 18 is positioned to have the filter segment 32 for the spectral range 1.4μm to 2.5μm positioned to have incident radiation projected therethrough. As earlier mentioned, when the subject invention is being operated in an Automatic mode, the filter wheel 18 would be rotating at a rate of two revolutions per minute. The gain of the amplifiers 48 and 50 would accordingly be reduced by approximately one half for a period of approximately eight to ten seconds in each successive 30-second interval. In the event that the invention is being operated in a Manual mode and filter segment 32 is positioned to have incident radiation projected therethrough, then the gain of the amplifiers 48 and 50 would remain decreased.

The multiplexer 42 is also connected to receive various temperature measurements including temperature measurements for the respective detectors 12 and 16 which may be provided by use of any conventional arrangement including a heater-cooler 56 and a temperature control circuit 58, which may include appropriate temperature sensors associated with the respective detectors 12 and 16 as may be required. A temperature sensor 60 is situated in the optical unit within the housing 2 for the purpose of providing a measurement of the temperature thereof. A fourth temperature sensor 62 also may be situation within the housing of the electronics unit for the purpose of providing a temperature indication of the chassis thereof. As shown, each of the temperature measurements are applied to the multiplexer 42 for timely recordation as is to be hereinafter discussed via a temperature monitor amplifying circuit 64 which may be a conventional amplifier that serves to provide appropriate electrical output signals representative of the respective temperature readings.

The encoder position circuit 55 is also connected to have the output signals thereof applied to a timing control circuit 57 which serves to provide timing control signals to the multiplexer 42 in accordance with the position of the filter wheel 18 as indicated by signals from the encoder 26. As earlier mentioned, when the subject invention is being operated in an Automatic mode, the filter wheel is continually rotated resulting in the successive passage of the opaque sections 34, 36 and 38 through the beam of incident radiation. Such opaque sections 34, 36 and 38 may be approximately thirty degrees in arcuate width. The period of time required for the opaque sections to rotate past the beam of incident radiation may thus be used to allow recordation of the various earlier mentioned measurements. As an example, a pair of such measurements may be recorded in the course of each opaque section being rotated past the incident beam of radiation. Besides the earlier mentioned temperatures of the respective detectors 12 and 16, and the electronics unit, additional measurements may include certain voltages being provided from the power supply 66. It has been found that two such measurements are readily recorded during the period required to permit an opaque section on the filter sheel 18 to pass through the beam of incident radiation.

The AC-to-DC converters 52 and 54 are operated in accordance with the timing signals provided by a sample and hold control circuit 68 which is connected to the chopper drive 70 such that timing signals provided from the sample and hold circuit 68 are synchronized with the operation of the chopper drive 70. The sample and hold control circuit may be a counter that is adapted to provide outputs at pre-selected time intervals. Each of the AC-to-DC converter circuits 52 and 54 may be conventional voltage converter circuits which for example may include relays and charging capacitors which are responsive to the timing signals provided from the sample and hold control circuit 68. Such timing signals are also provided from the sample and hold control circuit 68 to an analog-to-digital converter 72 which is connected to the output of the multiplexer 42 to convert the analog signals provided therefrom to a desired digital format. The digital signals provided from the converter circuit 72 may then be applied to a conventional tape recorder unit 74 which may be any of the known types of casette recorders. A digital formatter 76 may be connected to provide digital signals having a desired format to the recorder 74. For example, a serial or parallel format may be used. The digital formatter 76 may be any of the well known digital circuits that are available in the prior art.

A hand-held control unit 78 may be used in conjunction with the subject invention wherein a meter 80 is connected to provide readings of the various detectors and temperature sensors that were earlier discussed by being switched thereto via a conventional switch 82. The hand-held control unit may also include a lamp 84 such as a light emitting diode that is connected to be illuminated whenever the recordation of data is occurring. Also included on the hand control unit 78 may be a suitable switch that permits an operator to manually; turn the unit on and off.

A mode control circuit 87 including a bank of relays may be connected to permit the application of power from the power source 66 to pre-determined portions of the electronic circuitry. The power source 66 may include a six volt silver zinc battery with a capacity of 80 ampere hours. It is anticipated that four different modes may be used, including an Off mode, and a Standby mode in addition to the earlier mentioned Manual and Automatic modes. The Standby mode would involve power being applied to only the detector heater-coolers and pre-amplifiers to conserve power and extend the useful life of the power source 56 which may be a rechargeable battery of conventional type.

The manual mode may simply involve giving an operator the ability to manually control operation of the motor 22 and hence positioning of the filter wheel 18 by operation of a pair of switches 88 and 90. The switches 88 and 90 may be connected to control turning of the armature of motor 22 in either of two opposite directions via a conventional motor direction control circuit 92. The motor direction control circuit may be of any conventional type well known in the prior art to which AC power is provided. In this case AC power may be provided via a DC-to-AC voltage converter 94 which is appropriately connected to receive power via the mode control circuit 87.

In the Automatic mode, power would be applied to all of the electronic circuits including the motor 22 such that the filter wheel 18 is rotated at the earlier described rate. It is to be understood that although power connections to each of the respective electronic circuits has not been illustrated in FIG. 3 for the purpose of avoiding unnecessary cluttering of the drawings, such connections are well known in the prior art and may be accomplished in any conventional manner.

The digital data that is recorded may assume any of the many different formats imaginable. It has been found that the use of a 48 bit word format is satisfactory wherein selected groups of digits designate different information. For example, a complete 48 bit word may include a file number, the gain of the amplifiers 48 and 50, the encoder or filter wheel position, and the output signal level of the detectors 12 and 16. Recordation of data during the successive passage of the opaque sections 34, 36 and 38 may involve the same digital word being used for recordation of the earlier described miscellaneous measurements. For example, a 48 bit word may include the file number, encoder position and two miscellaneous measurements. Recordation of such data has been found useful in interpreting anomalies in the field.

Recordation of the encoder position may be readily accomplished by having the output of the encoder position circuit 55 applied to the recorder 74 or the amplifier 76 in any conventional manner for recordation. Similarly, a file number may be inserted for recordation via a file number control circuit 96 which may be a conventional counter adapted to be manually controlled to generate selected numbers that may be entered by manually manipulating a numbering device 98 and/or switch 100.

To summarize the field operation of the subject invention, the entire invention may be carried by one or two persons. To this end the recording electronics may be fabricated to be backpacked. The optical unit may be similarly fashioned. Once carried to a field location, the optical head may be mounted on a tripod about 1.3 meters above the ground surface with the long axis of the slit 20 oriented along the solar azimuth. The surface area covered to this height is approximately 200 cm$^2$. Gain settings for both amplifier-demodulator channels are made by manually setting the filter to approximately the 0.7$\mu$m position, the point of maximum signal observed on the hand-held meter. The response of the PbS detector is sufficiently flat that only one gain setting is required for the 0.4 to 1.4$\mu$m range. A spectrum of the surface may then be taken, followed immediately by measuring a standard such a Fiberfrax in the same orientation. Fiberfrax is a ceramic wool insulation that has a surface that is renewable by peeling the upper layer thereof and pressing it flat. When used as a standard, this is an important factor as inevitable contamination under field conditions can be eliminated or substantially avoided.

It has been found that it is possible to record 100 spectra on the two sides of a single digital tape cassette. With battery power sufficient to record about 700 spectra, an operation of about 2 – 3 days is possible being recharging is required.

The playback of recorded data may be accomplished with interface electronics which is capable of displaying the file number and accessing the beginning of any desired file. Such playback electronics may be adapted to operate the tape recorder within the portable electronics unit at a field headquarters. A digital-to-analog converter may be included for playback on a strip-chart recorder. Such a playback unit may also serve as a tape controller and interface to a computer that is used for analysis.

From the foregoing discussion, it is now clear that the subject invention provides a portable reflectance spectrometer that is particularly capable of being manually transported to remote field areas for use and which is capable of providing highly accurate data over a wide range of spectral wavelengths not heretofore able to be provided by any prior art device and which may be operated under a significantly useful range of temperature conditions.

While a preferred embodiment of the present invention has been described hereinabove, it is intended that all matter contained in the above description and shown in the accompanying drawings to be interpreted as illustrative and not in a limiting sense and that all modifications, constructions and arrangements which fall within the scope and spirit of the invention may be made.

What is claimed is:

1. A reflectance spectrometer comprising:

optical means for detecting incident radiation reflected by a target area, said optical means including:

first detector means or providing signals indicative of total incident radiance:

second detector means for providing signals indicative of predetermined spectral radiance;

beam splitter means for directing a portion of said incident radiation towards said first and second detector means;

filter means for filtering the portion of said incident radiation directed on said second detector means, said filter means being a circular variable filter;

means for varying the position of said filter means with respect to incident radiation;

recording means for recording said signals provided by said first and second detectors, said recording means including:

first and second amplifying means respectively connected to said first and second detector means for amplifying said said signals provided therefrom;

automatic gain control means automatically controlling the gain of said first and second amplifiers as a function of the wavelength of spectral radiation passed through said filter means;

digital recorder means for recording in digital form data represented by said signals from said first and second detectors;

voltage converter means for converting said signals from said first and second detectors from alternating current signals to direct current signals;

multiplexer means connected to said voltage converter means for selectively providing said signals from said first and second detectors for recordation by said digital recorder means; and digital means connected to said multiplexer means for providing output signals therefrom to said digital recorder for recordation thereby; and encoder means for providing encoder signals indicative of the position of said filter means with respect to incident radiation and the wavelength of spectral radiation passed through said filter means, said encoder signals being applied to said gain control means.

2. The reflectance spectrometer defined by claim 1 further including first temperature sensor means for providing first temperature signals indicative of the temperature of said optical unit;

second temperature sensor means for providing second temperature signals indicative of the temperature of said recording means;

third temperature sensor means for providing third temperature signals indicative of the temperature of said first detector means; and fourth temperature sensor means for providing fourth temperature signals indicative of the temperature of said second detector means, said temperature signals being applied to said multiplexer for application to said digital recorder means for recordation.

3. The reflectance spectrometer defined by claim 2 said circular variable filter including a plurality of filter segments and a plurality of opaque segments, each filter segment being separated by an opaque segment, said filter segment in combination permitting passage of radiation having a selected range of wavelengths, each of said filter segments being limited to a portion of said range of wavelengths, said reflectance spectrometer further including motor means for revolving said circular variable filter.

4. The reflectance spectrometer defined by claim 3, further including timing control means connected to receive said encoder signals for controlling said multiplexer means, said signals from said first and second detector means being provided for recordation by said multiplexer when said filter segments are positioned to have radiation passed therethrough, said temperature signals being selectively provided for recordation in accordance with the position of said filter means with respect to incident radiation.

5. The reflectance spectrometer defined by claim 3 further including chopper means for chopping said incident radiation.

6. The reflectance spectrometer defined by claim 5, said optical means further including means for controlling the temperature of said first and second detectors.

7. The reflectance spectrometer defined by claim 3 further including timing control means connected to receive said encoder signals for controlling said multiplexer means, said signals from said first and second detector means being provided for recordation by said multiplexer when said filter segments are positioned to have radiation passed therethrough, said temperature signals being selectively provided for recordation when an opaque segment is positioned to block passage of incident radiation to said second detector.

8. The reflectance spectrometer defined by claim 7 further including a power source having a rechargeable battery connected to provide power to said recording means.

9. The reflectance spectrometer defined by claim 8 wherein said optical means and said recording means each include housing means for permitting said optical means and said recording means to each be backpacked by a human being.

10. The reflectance spectrometer defined by claim 9 further including a hand-held meter for permitting the selective reading of preselected engineering data for predetermined conditions of said optical means and said recording means.

* * * * *